United States Patent
Larsson

[19]
[11] Patent Number: 5,954,690
[45] Date of Patent: Sep. 21, 1999

[54] ALTERNATING SUCTION BREASTPUMP ASSEMBLY AND METHOD

[75] Inventor: Michael N. Larsson, Baar, Switzerland

[73] Assignee: Medela Holding AG, Switzerland

[21] Appl. No.: 08/827,872

[22] Filed: Apr. 11, 1997

[30] Foreign Application Priority Data

Apr. 14, 1996 [EP] European Pat. Off. .............. 96105847

[51] Int. Cl.⁶ .................................................. A61M 1/06
[52] U.S. Cl. ............................................ 604/74; 604/152
[58] Field of Search ............................... 604/74–76, 120, 604/131, 151, 152; 417/534, 535, 536, 538

[56] References Cited

U.S. PATENT DOCUMENTS

| | | |
|---|---|---|
| 823,316 | 6/1906 | Andersen ............................ 119/14.07 |
| 1,184,293 | 5/1916 | Zeratsky . |
| 1,259,309 | 3/1918 | Somers . |
| 1,596,520 | 8/1926 | Eskholme et al. . |
| 3,238,937 | 3/1966 | Stein . |
| 3,382,867 | 5/1968 | Reaves . |
| 3,931,795 | 1/1976 | Duncan . |
| 3,990,816 | 11/1976 | Kohler et al. ........................... 417/536 |
| 4,263,912 | 4/1981 | Adams . |
| 4,486,157 | 12/1984 | Hayashi ................................. 417/534 |
| 4,607,596 | 8/1986 | Whittlestone et al. ............... 119/14.02 |
| 4,673,388 | 6/1987 | Schlensog et al. . |
| 4,857,051 | 8/1989 | Larsson . |
| 4,929,229 | 5/1990 | Larsson .................................... 604/74 |
| 4,941,433 | 7/1990 | Hanauer . |
| 4,964,851 | 10/1990 | Larsson .................................... 604/74 |
| 5,007,899 | 4/1991 | Larsson .................................... 604/74 |
| 5,076,769 | 12/1991 | Shao .................................. 417/535 X |
| 5,178,095 | 1/1993 | Mein . |
| 5,218,924 | 6/1993 | Thompson et al. . |
| 5,295,957 | 3/1994 | Aida et al. . |
| 5,304,129 | 4/1994 | Forgach . |
| 5,514,166 | 5/1996 | Silver et al. . |
| 5,571,084 | 11/1996 | Palmer .................................... 604/74 |
| 5,586,518 | 12/1996 | Carrano ............................... 119/14.51 |
| 5,601,531 | 2/1997 | Silver ...................................... 604/74 |
| 5,616,125 | 4/1997 | Jelks ....................................... 604/74 |
| 5,720,722 | 2/1998 | Lockridge ............................... 604/74 |
| 5,776,098 | 7/1998 | Silver et al. ............................. 604/74 |

FOREIGN PATENT DOCUMENTS

| | | |
|---|---|---|
| 0 123 269 A3 | 4/1984 | European Pat. Off. . |
| 0 733 376 A2 | 9/1996 | European Pat. Off. . |
| 33 28 725 A1 | 2/1984 | Germany . |
| 158 976 | 5/1957 | Sweden . |
| 0762701 | 12/1956 | United Kingdom . |
| 2 082 920 | 3/1982 | United Kingdom . |
| 2 127 293 | 4/1984 | United Kingdom . |

OTHER PUBLICATIONS

The Whittlestone Breastmilker, Model Havenwood, MK III Operating Manual.
Circle Caring Brochure, Ameda Egnell.
Medela Hospital Catalogue, pp. 20–21, 23–25.
Breastfeeding, A Guide For the Medical Professional, Ruth A. Lawrence, pp. 467–469.

*Primary Examiner*—Ronald Stright
*Assistant Examiner*—A. T. Nguyen
*Attorney, Agent, or Firm*—Brinks Hofer Gilson & Lione

[57] ABSTRACT

A double-breastpump assembly comprising first and second breastpump units. Each breastpump unit has a breast shield within which a breast is received. A vacuum pump unit for creating a periodic reduced air pressure is alternately applied within the breast shield of each breastpump unit.

12 Claims, 1 Drawing Sheet

ALTERNATING SUCTION BREASTPUMP ASSEMBLY AND METHOD

FIELD OF THE INVENTION

This invention relates to breastpumps for drawing, or expressing, breastmilk.

BACKGROUND OF THE INVENTION

Breastpumps for use by nursing mothers are well known. They allow the nursing woman to express the breastmilk as necessary or convenient, and further provide collection of breastmilk for later use. For some mothers, breastpumps may be a necessity, such as when the child has suckling problems. A breastpump may also be necessary for the mother who has problems with excessive or deficient milk production, or who has soreness, deformation or injury of the mammilla.

Breastpumps for single-breast pumping and double-breast pumping are both commonplace. Single-breastpumps by their nature pump only one breast at a time. Double-breastpumps have the advantage of pumping both breasts at the same time. Double-breastpumps typically are motor driven, being either battery or electrically driven.

In known equipment of this type, two breastpump shields are connected by air suction lines to a pressure chamber of a suction pump assembly. A low (or reduced) pressure is created inside the chamber by either a reciprocating piston, diaphragm or the like within the suction unit, thereby creating a suction (or vacuum) within the breastpump shields. In these types of known breastpumps, suction pressure is typically applied to the breasts only during the suction (intake or pull) stroke of the piston or diaphragm. In addition, known breastpumps of this type apply suction pressure to both breasts simultaneously (i.e., in "parallel"). This is ordinarily accomplished using a single output from the suction source which is then split between the two breastshields.

It has now been determined that alternating suction on the two breasts offers several advantages, including a significant reduction in the time required for breast pumping. Applicants are not aware of any breastpump in the prior art which has been developed for double-breast pumping which alternates a suction stroke on two breasts in double-pumping mode. It is known, however, to alternate a compression (increased pressure) stroke between two breasts being pumped, but with a continuous vacuum to the breasts, as shown in U.S. Pat. No. 4,607,596.

SUMMARY OF THE INVENTION

The present invention has a principal objective to provide a double-breastpump assembly and method comprising first and second breastpump units which are alternatively subjected to a suction stroke. In a preferred embodiment, each breastpump unit has a breast shield within which a breast is received.

A receptacle for collecting breastmilk expressed into the breast shields, and a conduit structure for conveying breastmilk from the breast shields to the receptacle, further comprises the breastpump unit.

Periodic reduced air pressure is alternatively created within the breast shield of the first and second breastpump units by a vacuum pump unit. In one contemplated form of the invention, a single vacuum pump generates the suction through the reciprocating action of a piston within a pump cylinder. As the piston is moved in one direction in the cylinder a negative pressure is generated in a first chamber of the cylinder which is communicated through tubing connected to the first chamber to one breastpump unit. The other or second chamber of the cylinder is simultaneously subjected to an increased pressure by the same movement. That increased pressure can be utilized in part to effect milk movement into a collection chamber of the other or second breastpump, but otherwise bled to the atmosphere through appropriate one-way valving.

When the piston is moved in the opposite direction, a negative pressure is now generated in the second chamber, which in turn is communicated to the other (second) breastpump unit through tubing connected to the second chamber. Likewise, an increased pressure is created in the first chamber, to be utilized or bled off in a like manner.

Instead of a reciprocating piston, a membrane or diaphragm can be used which is driven back and forth across an enclosure divided into two chambers by the membrane. Moreover, suction from a single vacuum source could be appropriately connected by valving in an alternating fashion to the breastpump units, or two vacuum sources could be used which are controlled to apply suction only alternately to the breasts.

These and other features and advantages of the present invention will be further understood and appreciated when considered in relation to the following detailed description of an embodiment taken in conjunction with the drawings, in which:

DETAILED DESCRIPTION OF A PREFERRED EMBODIMENT

Figure 1:
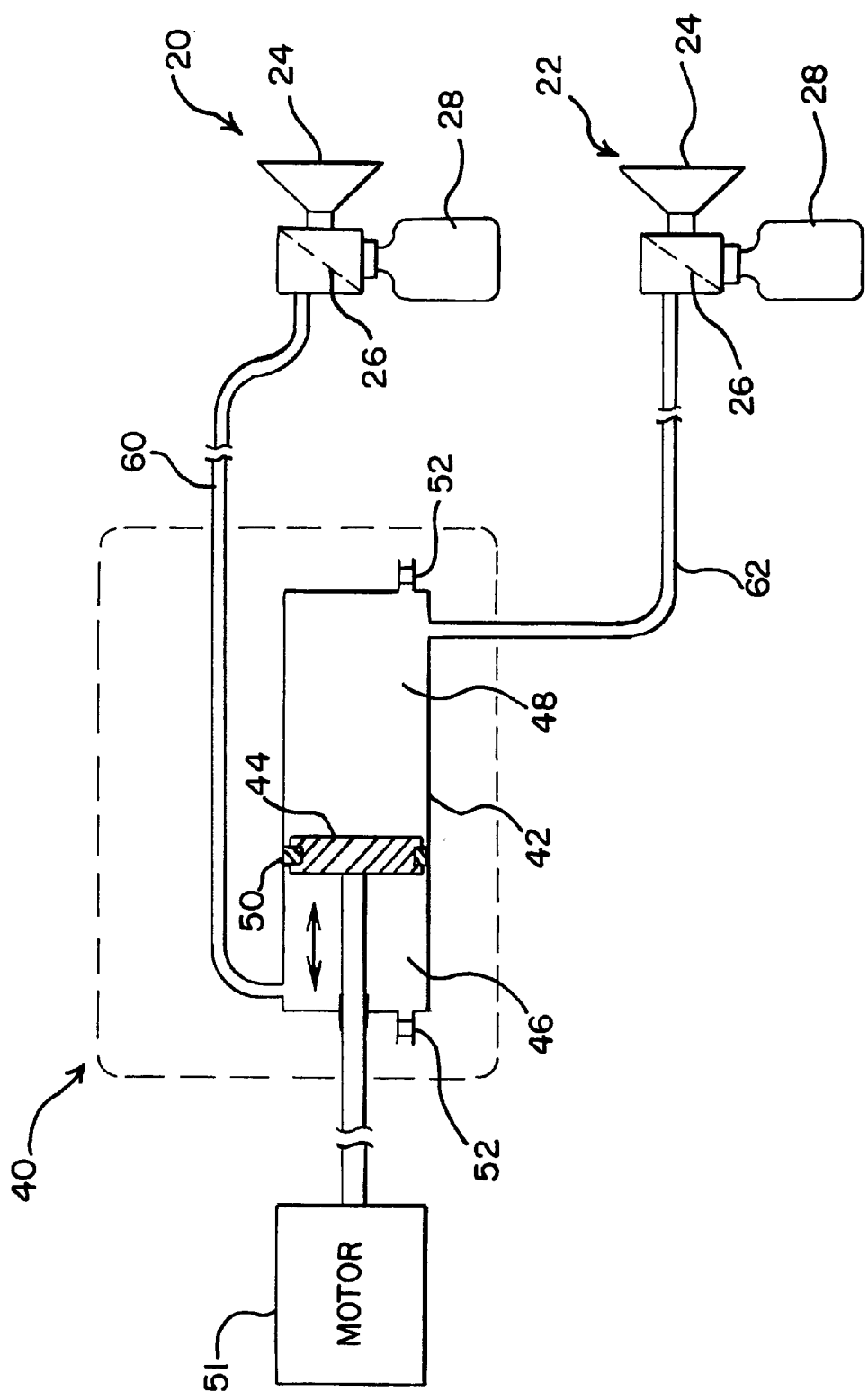
FIG. 1 is a schematic of a alternating suction breastpump assembly made in accordance with the teachings of this invention.

Referring to FIG. 1, a breastpump assembly of the present invention has two breastpump units 20, 22 and a vacuum pump unit 40. The suction pump unit 40 is shown separate from the breastpump units 20, 22. It could be made integral with a breastpump unit, however.

Each breastpump unit 20, 22 has a breast shield or hood 24 that is placed on the breast. Such a breastpump unit is shown in U.S. Pat. No. 4,929,229, for example, the disclosure of which is incorporated herein by reference. A vacuum or negative pressure is created within a breast shield 24, thereby drawing milk through a pulling force applied to the breast. The reduced air pressure is generated by the vacuum pump unit 40 and is conveyed to each breastpump unit by a respective airline (or suction line) 60, 62.

The suction pump unit 40 of the preferred embodiment comprises a dual-acting working cylinder 42 having a reciprocating piston 44. The piston 44 divides the interior volume of the working cylinder 42 into first and second air chambers, 46 and 48 respectively. An o-ring or a gasket 50 is located in a groove around the circumference of the piston 44, and creates an airtight seal with the interior sidewall of the cylinder 42, and between the first and second chambers 46, 48.

Reduced air pressure is alternately created in the first and second air chambers 46 and 48 by moving, or reciprocating, the piston 44 back and forth. For example, as the piston 44 is moved towards the first chamber 46, the air pressure is reduced in the second chamber 48. Conversely, as the piston 44 is moved towards the second chamber 48, the air pressure is reduced in the first chamber 46. The increased air pressure that is created in the chamber, 46 or 48, towards which the piston 44 is moved is released through a check valve 52 connected to that chamber, such as a one-way flap valve.

The piston 44 may be reciprocated manually, or more preferably by motor-driven actuation 51 well known in the art. Motor-driven actuation of the piston 44 may be electrically or battery powered.

It should be understood that the working or pump cylinder 42 of the suction pump unit 40 can be of any shape, such as a round or square tube cross-section for example, so long as the piston is shaped accordingly (i.e., has a shape that corresponds with the interior shape of the cylinder or tube). It should also be understood that the vacuum pump unit 40 may comprise more than one working cylinder 42. For example, the vacuum pump unit may comprise two separate working cylinders which are alternately applied to generate a periodic reduced air pressure in a respective breastpump unit.

The suction pump unit may also comprise an interior volume which is divided by a flexible diaphragm into two separate air chambers. The flexible diaphragm is moved, or reciprocated, back and forth to create an alternating periodic reduced air pressure inside the two chambers.

Referring again to FIG. 1, an airline 60 is connected from the first air chamber 46 of the suction pump unit 40 to the first breastpump unit 20 such that the reduced air pressure created in the first air chamber 46 is conveyed to the first breastpump unit 20, thereby creating a reduced air pressure (suction or vacuum) within the breast shield 24 of the first breastpump unit 20. The second air chamber 48 is connected to the second breastpump unit 22 by a separate airline 62 such that the reduced air pressure created in the second air chamber 48 is conveyed to the second breastpump unit 22, thereby creating a reduced air pressure (suction or vacuum) within the breast shield 24 of the second breastpump unit 22. Consequently, a periodic reduced air pressure is alternately created within the breast shield 24 of each breastpump unit 20, 22.

Each breastpump unit 20, 22 includes a valve 26, such as a check valve, which closes when a reduced air pressure is conveyed by the vacuum pump unit 40 to the breastpump unit 20, 22. When the reduced air pressure conveyed to the breastpump unit 20, 22 terminates or is relieved, then the valve 26 opens to allow the air pressure within the breast shield 24 to return to normal or ambient air pressure, thereby releasing the vacuum or suction applied to the breast. For example, as the piston 44 of the vacuum pump unit 40 moves towards the first chamber 46, the reduced air pressure within the first chamber 46 (which was created when the piston was previously moving towards the second chamber 48) is relieved, and any increased air prsesure is released through a check valve 52. At the same time, valve 26 in the first breastpump unit 20 opens to release the vacuum within the breast shield 24, and any overpressure that may be generated. As the piston 44 of the vacuum pump unit 40 then moves back towards the second chamber 48, the reduced air pressure within the second chamber 48 is now relieved, and any increased air pressure is released through a check valve 52 in that chamber. At this time, valve 26 in the second breastpump unit 20 opens to release the vacuum within the breast shield 24.

Milk is drawn from the breast by the reduced air pressure created within a breast shield 24. The breastmilk expressed into the breast shield 24 is collected by one or more milk receptacles 28. Each breastpump unit 20, 24 includes a separate milk receptacle 28.

Certain details relating to the basic construction and operation of the preferred double-breastpump assembly which are well known in the art have therefore been omitted. Many of these details, particularly those relating to the construction and operation of the breastpump units, are disclosed in U.S. Pat. No. 4,929,229, which again is incorporated by reference herein.

Thus, while an embodiment of the present invention has been described herein, those with skill in this art will recognize changes, modifications, alterations and the like which still shall come within the spirit of the inventive concept, and such are intended to be included within the scope of the invention as expressed in the following claims.

What is claimed is:

1. A double-breastpump assembly comprising:

first and second breastpump units, each breastpump unit having a breast shield within which a breast is received, a receptacle for collecting breastmilk expressed into said breast shield, and a conduit structure connecting said breast shield to said receptacle for conveying breastmilk from said breast shield to said receptacle;

a vacuum pump unit having first and second air chambers defined by a movable member within an enclosure, in which a periodic reduced air pressure is alternately created in each said chamber;

a first airline connecting said first air chamber to said first breastpump unit for conveying said periodic reduced air pressure from said first air chamber to said first breastpump unit;

a second airline connecting said second air chamber to said second breastpump unit for conveying said periodic reduced air pressure from said second air chamber to said second breastpump unit; and a valve associated with each of said first and second chambers for exhausting increased air pressure within a respective chamber to ambient air during the period that said periodic reduced air pressure is being created in said breast shield of the other breastpump units.

2. A double-breastpump assembly comprising:

first and second breastpump units, each breastpump unit having a breast shield within which a breast is received;

a vacuum pump unit having first and second air chambers in which a periodic reduced air pressure is alternately created, said first chamber being connected to said breast shield of said first breastpump unit such that said periodic reduced air pressure is conveyed from said first air chamber to said breast shield of said first breastpump unit, said second chamber being connected to said breast shield of said second breastpump unit such that said periodic reduced air prsssure is conveyed from said second air chamber to said breast shield of said second breastpump unit;

means for conveying said reduced air pressure to each said breastpump unit;

at least one receptacle for collecting breastmilk expressed into said breast shield; and a conduit structure connecting said breast shields to said receptacle for conveying breastmilk from said breast shields to said receptacle.

3. The double-breastpump assembly of claim 2 wherein said first and second air chambers are connected to said breast shields of said first and second breastpump units by respective airlines.

4. The double-breastpump assembly of claim 2 wherein said vacuum pump comprises a reciprocating piston within a pump cylinder, said periodic reduced air pressure being created in first and second air chambers defined by said reciprocating piston within said cylinder.

5. The double-breastpump assembly of claim 4 wherein said reciprocating piston is motor driven.

6. The double-breastpump assembly of claim 4 wherein said first and second breastpump units each further include a valve for returning the air pressure within a respective breast shield to ambient during the period that a reduced air pressure is being created within the other breast shield.

7. A method for double-breastpumping comprising the steps of:
- providing first and second breastpump units, each breastpump unit having a breast shield within which a breast is received;
- providing a receptacle for collecting breastmilk expressed into said breast shield, and a conduit structure connecting said breast shield to said receptacle for conveying breastmilk from said breast shields to said receptacle;
- providing a vacuum pump unit having an enclosure defining first and second air chambers;
- driving a movable member in reciprocating fashion within said enclosure to change the volume of each of said chambers in alternating fashion to thereby generate a periodic reduced air pressure alternately in each chamber;
- providing a first airline connecting said first air chamber to said first breastpump unit and conveying said periodic reduced air pressure from said first air chamber to said first breastpump unit such that a periodic suction is created within said breast shield of said first breastpump unit;
- providing a second airline connecting said second air chamber to said second breastpump unit for conveying said periodic reduced air pressure from said second air chamber to said second breastpump unit such that a periodic suction is created within said breast shield of said second breastpump unit; and
- providing and operating valves for controlling air pressure within each of said breast shields.

8. A double-breastpump assembly comprising:
- first and second breastpump units, each breastpump unit having a breast shield within which a breast is received;
- at least one receptacle for collecting breastmilk expressed into the breast shields;
- a conduit structure connecting said breast shields to said receptacle for conveying breastmilk from said breast shields to said receptacle;
- a vacuum pump unit having first and second air chambers in which a reduced air pressure is alternately created;
- a first airline connecting said first air chamber to said first breastpump unit for conveying air pressure changes from said first air chamber to said breast shield of said first breastpump unit;
- a second airline connecting said second air chamber to said second breastpump unit for conveying air pressure changes from said second air chamber to said breast shield of said second breastpump unit;
- whereby reduced air pressure is alternately created in each said breastpump unit.

9. The double-breastpump assembly of claim 8 wherein said vacuum unit further comprises a reciprocating piston within a piston cylinder for creating said alternating reduced air pressure in said first and second air chambers.

10. The double-breastpump assembly of claim 9 further comprising a valve for releasing any air pressure changes conveyed to a breast shield other than a reduced air pressure.

11. A method for double-breastpumping, comprising the steps of:
- providing first and second breastpump units, each breastpump unit having a breast shield within which a breast is received;
- providing at least one receptacle for collecting breastmilk expressed into said breast shields, and a conduit structure connecting said breast shields to said receptacle for conveying breastmilk from said breast shields to said receptacle; and
- generating a periodic reduced air pressure alternately within said breast shields of the first and second breastpump units so that a suction force is applied to each breast in alternating fashion;
- wherein said reduced air pressure is provided by a vacuum unit comprising first and second air chambers in which a periodic reduced air pressure is alternately created, said first chamber being connected to said breast shield of the first breastpump unit such that said periodic reduced air pressure is conveyed from said first air chamber to said breast shield of said first breastpump unit, and said second chamber is connected to said breast shield of said second breastpump unit such that said periodic reduced air pressure is conveyed from said second air chamber to said breast shield of said second breastpump unit.

12. The method of double-breastpumping of claim 11 wherein said vacuum unit further comprises a reciprocating piston, wherein said periodic reduced air pressure is created in said first and second air chambers by said reciprocating piston.

* * * * *